United States Patent [19]

Gednalske et al.

[11] Patent Number: 5,719,102
[45] Date of Patent: *Feb. 17, 1998

[54] METHOD FOR REDUCING ODOR FROM A HERBICIDAL MIXTURE

[75] Inventors: Joe V. Gednalske, River Falls, Wis.; Robert W. Herzfeld, Stillwater, Minn.

[73] Assignee: Cenex/Land O'Lakes Agronomy Company, Inver Grove Heights, Minn.

[*] Notice: The term of this patent shall not extend beyond the expiration date of Pat. No. 5,463,180.

[21] Appl. No.: 545,303

[22] Filed: Oct. 19, 1995

Related U.S. Application Data

[63] Continuation-in-part of Ser. No. 149,179, Nov. 5, 1993, Pat. No. 5,463,180.

[51] Int. Cl.$^6$ .......................... A01N 25/30; A01N 25/32; A01N 43/40; A01N 57/02
[52] U.S. Cl. .......................... 504/116; 504/206; 504/258
[58] Field of Search .......................... 504/116, 258, 504/206

[56] References Cited

U.S. PATENT DOCUMENTS

| | | | |
|---|---|---|---|
| 4,436,547 | 3/1984 | Sampson | 71/76 |
| 4,557,751 | 12/1985 | Ronning et al. | 71/91 |
| 4,971,630 | 11/1990 | Skaptason | 71/117 |
| 5,463,180 | 10/1995 | Gednalske et al. | 504/323 |

OTHER PUBLICATIONS

*The Agrochemicals Handbook*, 3rd Ed.; Kidd et al. (editor); Royal Society of Chemistry; (1991).

*McCutcheon's Emulsifiers & Detergents*; McCutcheon Publishing Co.; (1990); p. 192.

Puritch, George S.; *Pesticidal Soaps and Adjuvants—What are They and How do They Work?*, 23rd Annual Lower Mainland Horticultural Improvement Association Growers' Short Course; Feb. 11–12, (1981); pp. 53–67.

Van Valkenburg, J. Wade; *Adjuvants for Herbicides*; (1979); pp. i–ii, 1–8.

*Primary Examiner*—S. Mark Clardy
*Attorney, Agent, or Firm*—Kinney & Lange, P.A.

[57] ABSTRACT

A method for reducing odor of an odoriferous herbicide is described. The method includes providing a nonionic surfactant blend. The nonionic surfactant blend has an effective concentration of an acidulated soybean soapstock and an effective concentration of nonoxynol. The method also includes mixing the nonionic surfactant blend with the odoriferous herbicide.

9 Claims, No Drawings

METHOD FOR REDUCING ODOR FROM A HERBICIDAL MIXTURE

REFERENCE TO RELATED APPLICATION

This application is a continuation-in-part of U.S. patent application Ser. No. 08/149,179, filed Nov. 5, 1993 now U.S. Pat. No. 5,463,180.

BACKGROUND OF THE INVENTION

The present invention relates to using a mixture of a nonionic surfactant blend having an acidulated soybean soapstock component with a compatible herbicide to reduce an objectionable odor of the herbicide.

Liquid herbicides and dry, flowable herbicides are mixed with water to more economically apply the herbicides to crops. However, liquid and dry herbicides, even when mixed in water, have a limited capacity to pass through a leaf surface and then to translocate within a weed. A surfactant is added to the liquid and dry, flowable herbicides to help the herbicides enter the leaf surface of the weed. Once the herbicide enters a leaf surface of a weed, the herbicide can be translocated to an action site within the weed and can kill the weed.

Surfactants are also used to disperse herbicides in water. The surfactants include a lipophilic portion compatible with many herbicides and a hydrophilic portion compatible with water. Depending upon the herbicide, the surfactant used is suitably either ionic or nonionic.

Ionic surfactants include a molecular structure having a charge on the hydrophilic portion of the structure. Ionic surfactants having a positive charge are cationic surfactants. Ionic surfactants having a negative charge are anionic surfactants.

Nonionic surfactants include a molecular structure where the nature of chemical bonds within the structure impart hydrophilic and lipophilic features to the surfactant. Nonionic surfactants do not have a net charge. Nonionic surfactants are usually products of a petrochemical process. Consequently, the nonionic surfactants tend to be expensive and to have limited environmental compatibility.

Surfactants interact with herbicides in a number of ways both before and after application to a crop. In addition to having use as an emulsifier, a surfactant may act as a penetrant, spreader, sticker, stabilizer, wetting agent, dispersant and defoamer. The surfactant may affect a rate of drying of a droplet on a plant and the nature of a residue, liquid or crystal. The surfactant may influence the weathering characteristics of the herbicide, including rewetting characteristics.

Surfactants have not typically had an effect on odor of herbicides when blended with herbicides. An unpleasant odor emitted by many herbicides has tended to restrict the use of these herbicides. For instance, a herbicide, 2,4-dichlorophenoxy acetic acid (2,4-D), has use in killing broadleaf weeds. Unfortunately, 2,4-D emits an unpleasant odor. The odor discourages use of 2,4-D in suburban areas.

SUMMARY OF THE INVENTION

The present invention includes a method for reducing odor of herbicides that includes providing a nonionic surfactant blend that includes an effective amount of an acidulated soybean soapstock and a nonionic surfactant, providing an odoriferous herbicide and water in quantities effective to kill weeds, and adding the nonionic surfactant blend to the herbicide and water in a concentration of approximately 2.0 to 5.0 percent by volume to make a homogeneous herbicidal adjuvant mixture.

DETAILED DESCRIPTION OF THE PREFERRED EMBODIMENTS

The present invention includes a method for reducing odor of a herbicide and a reduced odor herbicidal mixture. The reduced odor herbicidal mixture includes a nonionic surfactant blend, an odoriferous herbicide, and water. The nonionic surfactant blend includes the components of the acidulated soybean soapstock and a nonionic surfactant, nonoxynol. The blend preferably also includes a viscosity reducing agent, water, and an antifoam agent.

The method of the present invention includes providing and mixing components in a particular order to make a nonionic surfactant blend that is homogeneous. The method for making the nonionic surfactant blend of the present invention includes providing the ingredient of nonoxynol in an effective concentration range. Preferably, the concentration of nonoxynol ranges from approximately 38 to 80 percent by volume of the nonionic surfactant blend. The effective concentration range is determined by the performance of the concentration in promoting translocation of a compatible herbicide in a weed and by cost of the concentration. The concentration of nonoxynol is preferably approximately 59.5 percent by volume.

The method also includes providing the acidulated soybean soapstock in an effective concentration. The effective concentration of acidulated soybean soapstock ranges from approximately 10 to 30 percent by volume. Preferably, the concentration of acidulated soybean soapstock is approximately 20 percent by volume of the nonionic surfactant blend. The effective concentration of acidulated soybean soapstock is determined by the performance of the concentration to promote translocation of a compatible herbicide in a weed and by solubility of the acidulated soybean soapstock in the nonionic surfactant blend.

The method also includes providing a viscosity reducing agent in an effective concentration. Preferred viscosity reducing agents include isopropanol and n-butanol. The effective concentration ranges from approximately 5 to 10 percent by volume of the nonionic surfactant blend for either isopropanol or n-butanol. The concentration is preferably approximately 10 percent by volume. The effective concentration reduces viscosity of the nonionic surfactant blend to a viscosity that promotes ease of handling of the nonionic surfactant blend.

The method also includes providing water in an effective concentration that preferably ranges from approximately 5 to 10 percent by volume of the nonionic surfactant blend. The effective concentration of water reduces cost of using the blend without reducing performance of the blend.

Preferably, the method for making the nonionic surfactant blend also includes providing an antifoam agent such as Dow Corning A Antifoam manufactured by Dow Chemical of Midland, Michigan. The antifoam agent is preferably provided at a concentration of approximately 0.5 percent by volume of the nonionic surfactant blend.

The nonionic surfactant method may also optionally include a fatty acid ethoxylate of up to approximately 20 percent by volume of the nonionic surfactant blend. Preferred concentration ranges for components provided and mixed to make the nonionic surfactant blend are described in Tables 1 and 2.

Most preferably, the nonionic surfactant blend is made by adding an effective concentration of nonoxynol to water.

Then an effective concentration of viscosity reducing agent is added to the nonoxynol-water dispersion. In a next step, the acidulated soybean soapstock is added and mixed with the nonoxynol-viscosity reducing agent dispersion. Then, antifoam agent, such as Dow Corning A Antifoam, is added to the dispersion.

The mixing order illustrated in Table 1 is the most preferred in the manufacture of the nonionic surfactant blend. Once mixed, the nonionic surfactant blend may be stored at any ambient temperature without changing consistency or activity.

TABLE 1

| % By Vol. | Ingredients | Mixing Order |
|---|---|---|
| 59.5 | Nonoxynol | 1 |
| 10.0 | Water | 2 |
| 10.0 | Viscosity Reducing Agent | 3 |
| 20.0 | Acidulated Soybean Soapstock | 4 |
| 0.5 | Dow Corning a Antifoam | 5 |

In another embodiment, the nonionic surfactant, nonoxynol, additionally includes a fatty alcohol ethoxylate. The mixing order for the nonionic surfactant including the fatty alcohol ethoxylate is described in Table 2. The ingredients and quantities described in Tables 1 and 2 are also effective for reducing odor of herbicides when blended with the herbicides.

TABLE 2

| % By Vol. | Ingredients | Mixing Order |
|---|---|---|
| 38.6–49.5 | Nonoxynol | 1 |
| 10–20 | Fatty Alcohol Ethoxylate | 2 |
| 5–10 | Water | 3 |
| 5–10 | Viscosity Reducing Agent | 4 |
| 10–30 | Acidulated Soybean Soapstock | 5 |
| 0.2–0.5 | Anti-foam | 6 |

The acidulated soybean soapstock component that is provided and mixed to make the nonionic surfactant blend is a brown liquid and has a specific gravity of approximately 0.95. The acidulated soybean soapstock is highly viscous. To reduce the viscosity, the acidulated soybean soapstock is heated to a minimum temperature of approximately 72° F. prior to mixing with other ingredients of the nonionic surfactant blend.

Even when heated, the high viscosity of the acidulated soybean soapstock limits the effective concentration of acidulated soybean soapstock to not more than approximately 30 percent by volume of the total nonionic surfactant blend. The high viscosity of the acidulated soybean soapstock may cause handling problems if the concentration by volume exceeds 30 percent. The concentration of the acidulated soybean soapstock is preferably less than approximately 20 percent by volume of the nonionic surfactant blend.

The acidulated soybean soapstock used in the blend of the present invention is formed by the complete acidulation of soybean soapstock. Soybean soapstock is a by-product of the alkali refining of soybean oil. In soybean oil processing, crude soybean oil is treated with dilute sodium hydroxide. In other acceptable embodiments, the crude soybean oil is treated with soda ash or a combination of sodium hydroxide and soda ash. The sodium hydroxide and soda ash react with free fatty acids in the crude soybean oil fraction to neutralize the free fatty acids and to form a soapstock. The soapstock is typically separated from the oil by centrifugation or settling. The soapstock is then treated with sulfuric acid in an acidulation step.

Soybean soapstock is approximately 6 percent of the total volume of crude soybean oil refined. The free fatty acids in acidulated soybean soapstock are typically less than one percent of the total volume of crude soybean oil refined. Soybean soapstock is also called "foots" since the soapstock accumulates in the bottom of a refining tank. Acidulated soybean soapstock is regarded as a relatively unrefined waste product of soybean oil processing, having only limited commercial use by soap manufacturers and animal feed producers.

A contract grade of acidulated soybean soapstock preferably includes not less than 85 percent total fatty acids by volume. Most preferably, the acidulated soybean soapstock used in the blend of the present invention includes a total fatty acid concentration range of approximately 94 to 96 percent by volume as shown in Table 3. The acidulated soybean soapstock also includes a moisture concentration of not more than approximately 5 percent by volume. One typical analysis of acidulated soybean soapstock for use in the present invention, manufactured by the Honeymead Products Company of Mankato, Minn., is described in Table 3. One typical analysis of a fatty acid profile for acidulated soybean soapstock for use in the present invention is shown in Table 4.

TABLE 3

| Acid Value | 80–130 |
|---|---|
| Total Fatty Acids | 94%–96% |
| Color | Dark |
| Iodine Value | 118–130 |
| Moisture (Karl-Fischer) | 5% max |

TABLE 4

| FATTY ACID PROFILE | % OF TOTAL FATTY ACIDS |
|---|---|
| 14:0 myristic acid | 0.1 |
| 16:0 palmitic acid | 14.1 |
| 18:0 stearic acid | 4.8 |
| 18:1 oleic acid | 21.0 |
| 18:2 linoleic acid | 52.2 |
| 18:3 linolenic acid | 6.9 |
| 20:0 arachidic acid | 0.3 |
| 22:0 behenic acid | 0.4 |

All testing was performed by approved American Oil Chemists Society methods.

The nonoxynol component of the nonionic surfactant blend is described in U.S. Pat. No. 2,313,477. The nonoxynol is also known by chemical names that include α-(nonylphenyl)-ω-hydroxypoly(oxy-1,2-ethanediyl); polyethyleneglycol ether; mono(nonylphenyl)ether; macrogol nonylphenyl ether; polyoxyethylene(n)-nonylphenyl ether; nonylphenyl polyethyleneglycol ether; nonylphenoxypolyethoxyethanol; and poly(oxy-1,2 ethanediyl)-α-(nonphyenol)-Ω-hydroxy, CAS Registry No. 0009016-45-9. The nonoxynol has a chemical formula,

$$C_9H_{19}-(OCH-_2CH_2)_nOH$$

The "n" of the chemical formula preferably ranges from 8 to 10 carbon atoms. The "n" is most preferably 9 carbon atoms. The nonoxynol provided to the blend of the present invention preferably includes approximately 100 percent nonoxynol by volume. However, the nonoxynol added may acceptably include a fatty acid ethoxylate in a concentration of up to 20 percent by volume to form a nonoxynol-ethoxylate solution.

The nonionic surfactant blend includes ingredients of nonoxynol, acidulated soybean soapstock, a viscosity reducing agent such as isopropanol or n-butanol, and water in effective concentration ranges. Effective ranges include approximately 38 to 80 percent by volume for nonoxynol, approximately 10 to 30 percent for acidulated soybean soapstock, approximately 5 to 10 percent for viscosity reducing agent, and approximately 5 to 10 percent for water. The nonionic surfactant blend also acceptably includes fatty alcohol ethoxylate and antifoam in effective concentration ranges. The ranges include approximately 10 percent to 20 percent by volume for adding fatty alcohol ethoxylate and approximately 0.2 to 0.5 percent by volume for antifoam.

The acidulated soybean soapstock is provided and mixed with the nonionic surfactant blend to replace a portion of the nonoxynol used in an application such as a herbicide dispersion. A benefit of replacing a portion of nonoxynol with acidulated soybean soapstock is a reduced cost of using the nonionic surfactant blend. Another advantage of replacing a portion of nonoxynol for acidulated soybean soapstock is an improved environmental compatibility. Acidulated soybean soapstock, unlike nonoxynol, is utilized as an animal food and is biodegradable.

The nonionic surfactant blend is combined with a compatible herbicide to form an improved herbicidal mixture. The herbicide concentration of the mixture is applied to a field at a concentration that acceptably ranges from approximately 0.004 to 2 pounds per acre. The preferred concentration depends upon the herbicide combined to make the mixture. The herbicidal mixture is acceptably supplemented with nitrogen. Nitrogen is acceptably added as urea ammonium nitrate (UAN) in a preferred concentration of up to approximately 28 percent by weight as nitrogen. The nonionic surfactant blend of the present invention is acceptably added to the improved herbicidal mixture at a concentration within the range of approximately 0.125 to 1 percent by volume. The remaining volume of the improved herbicidal mixture is comprised of water. The improved herbicidal mixture is preferably applied to the soil as a spray. However, any conventional method of application is suitable for use in the present invention.

The nonionic surfactant blend of the present invention is compatible with a wide variety of compatible herbicides that include nicosulfuron DF manufactured by DuPont and has the chemical name 2(((4,6-Dimethoxypyrimidin-2-yl) aminocarbonyl)aminosulfonyl)-N,N-dimethyl-3-pyridinecarboxamide; primisulfuron made by Ciba-Geigy having chemical name 3-[4,6-Bis-(difluoromethoxy)-pyrimidin-2-yl)-1-(2-methoxycarbonylphenylsulfonyl) urea; clethodim; fluazifop having chemical name 2-[4[[5-(trifluoromethyl)-2-pyridinyl]oxy]phenoxy]propanoic acid; quizalofop; sethoxydim having chemical name 2-[1-(ethoxyimino)butyl]-5-[2-(ethylthio)propyl]- 3-hydroxy-2-cyclohexen-1-one; imazethapyr having chemical name 2-[4, 5-dihydro-4omethyl-4-(1-methylethyl)-5-oxo-1 H-imidazole-2-yl]-3-pyridinecarboxylic acid; fomesafen; acifluorfen having chemical name 5-[2-chloro-4-(trifluoromethyl)-phenoxy]-2-nitrobenzoic acid; laptofen; bentazon having chemical name 3-isopropyl-1 H-2,1,3-benzothiadiazin-4-(3 H)-1,2,2-dioxide; trifensulfuron having chemical name methyl 3-[[[[(4-methoxy-6-methyl-1,3, 5-triazin-2-yl)amino]carbonyl]amino]sulfonyl]-2-thiophenecarboxylate; chlorimuron made by DuPont and having chemical name 2-[[[[(4-chloro-6-methoxypyrimidin-2-yl)amino]-carbonyl]amino]sulfomyl]benzoate; imazaquine; paraquat having chemical name 1,1'-dimethyl-4,4'-bipyridinium; glyphosate having chemical name N-(phosphonomethyl)glycine; tribenuron; chlorsulfuron having chemical name 3-(2-chloro-9 H-thioxanthen-9-ylidene)-N,N-dimethyl-1-propanamine, metsulfuron, 2,4-dichlorophenoxy acetic acid, fluazifop-P-butyl, and sulfosate.

The nonionic surfactant blend component of the herbicidal mixture maintains an adequate reduction in surface tension for good herbicide coverage and also aids in herbicide uptake.

The present invention also includes a substantially odor-free method for killing weeds that includes providing an effective concentration of an acidulated soybean soapstock, providing an effective concentration of the nonionic surfactant, nonoxynol and adding the acidulated soybean soapstock to the nonionic surfactant to form a nonionic surfactant blend, providing a herbicide and water in quantities effective to kill weeds, mixing the homogeneous blend with the herbicide to form a homogeneous herbicidal mixture and applying the herbicidal mixture to weeds. The effective quantities of components of the nonionic surfactant blend is described in Tables 1 and 2.

In addition to increasing herbicide performance, it has surprisingly been found that the nonionic surfactant blend of the present invention reduces the odor of herbicides, such as fluazifop-P-butyl and sulfosate, when mixed with the herbicide. Reduction of odor permits a use of these herbicides in suburban locations where odors are objectionable to neighbors.

The examples presented are intended to illustrate the performance of the improved nonionic surfactant blend and not to limit the methods and blend of the present invention.

EXAMPLE 1

The effectiveness of the nonionic surfactant blend at reducing the odor of fluazifop-Pobutyl (FUSILADE®, Zeneca Agricultural Products, Inc. of Fresno, Calif.) was examined. The nonionic surfactant blend was prepared according to the protocol set forth in Table 1. In particular, the nonionic surfactant blend contained nonoxynol, water, isopropanol, acidulated soybean soapstock, and Dow Corning A Antifoam.

Nonoxynol was first added to water to form a nonoxynol-water dispersion. The concentration of nonoxynol was approximately 59.5 percent by volume of the nonionic surfactant blend. The concentration of water was approximately 10.0 percent by volume of the nonionic surfactant blend. Isopropanol was then added to the dispersion at a concentration of approximately 10.0 percent by volume of the nonionic surfactant blend. Next, acidulated soybean soapstock was added to the dispersion at a concentration of approximately 20.0 percent by volume of the nonionic surfactant blend. Finally, Dow Corning A Antifoam was added to the dispersion at a concentration of approximately 0.5 percent by volume of the nonionic surfactant blend. The dispersion was then thoroughly mixed to form the nonionic surfactant blend.

Prior to application of the fluazifop-P-butyl to the crop, a herbicidal mixture was created by adding the nonionic surfactant blend to fluazifop-P-butyl at a concentration of approximately 1 percent by volume of the herbicidal mixture. Addition of the nonionic surfactant blend to fluazifop-P-butyl greatly reduced the odor of the fluazifop-P-butyl.

The herbicidal mixture was then diluted to the desired concentration with water. The diluted herbicidal mixture was then sprayed over the crop using conventionally known techniques at a rate of approximately 24 ounces of fluazifop-P-butyl per acre. While the diluted herbicidal mixture was being applied to the crop, it was noted that odor was greatly reduced when compared to applying fluazifop-P-butyl without the nonionic surfactant blend. The odor of the fluazifop-P-butyl also remained low after the diluted herbicidal mixture was applied to the crop.

EXAMPLE 2

The effectiveness of the nonionic surfactant blend at reducing the odor of sulfosate (TOUCHDOWN®, Zeneca Agricultural Products, Inc. of Fresno, California) was also examined. The nonionic surfactant blend was prepared according to the procedure set forth in Example 1.

Prior to application of the sulfosate to the crop, a herbicidal mixture was created by adding the nonionic surfactant blend to sulfosate at a concentration of approximately 1 percent by volume of the herbicidal mixture. Addition of the nonionic surfactant blend to sulfosate greatly reduced the odor of the sulfosate.

The herbicidal mixture was then diluted to the desired concentration with water. The diluted herbicidal mixture was then sprayed over the crop using conventionally known techniques at a rate of approximately 32 ounces of sulfosate per acre. While the diluted herbicidal mixture was being applied to the crop, it was noted that odor was greatly reduced when compared to applying sulfosate without the nonionic surfactant blend. The odor of the sulfosate also remained low after the diluted herbicidal mixture was applied to the crop.

Although the present invention has been described with reference to preferred embodiments, workers skilled in the art will recognize that changes may be made in form and detail without departing from the spirit and scope of the invention.

What is claimed is:

1. A method for reducing odor in a herbicide comprising:

providing an odor reducing effective amount of a nonionic surfactant blend having an effective amount of an acidulated soybean soapstock and an effective amount of nonoxynol; and mixing the nonionic surfactant blend with an odoriferous herbicide.

2. The method of claim 1 wherein the odoriferous herbicide is fluazifop-P-butyl.

3. The method of claim 1 wherein the odoriferous herbicide is sulfosate.

4. A herbicidal mixture comprising an odor reducing effective amount of an odoriferous herbicide and an effective amount of the nonionic surfactant blend, the nonionic surfactant blend comprising an effective amount of nonoxynol and an effective amount of acidulated soybean soapstock.

5. The herbicidal mixture of claim 4 wherein the odoriferous herbicide is fluazifop-P-butyl.

6. The herbicidal mixture of claim 4 wherein the odoriferous herbicide is sulfosate.

7. A method for applying to vegetation an odoriferous herbicide in a reduced odor state, the method comprising applying the herbicide to the vegetation in a nonionic surfactant blend having an odor reducing effective amount of acidulated soybean soapstock and an odor reducing effective amount of nonoxynol.

8. The method of claim 7 wherein the odoriferous herbicide is fluazifop-P-butyl.

9. The method of claim 7 wherein the odoriferous herbicide is sulfosate.

* * * * *

UNITED STATES PATENT AND TRADEMARK OFFICE
CERTIFICATE OF CORRECTION

PATENT NO. : 5,719,102

DATED : FEBRUARY 17, 1998

INVENTOR(S) : JOE V. GEDNALSKE, ROBERT W. HERZFELD

It is certified that error appears in the above-identified patent and that said Letters Patent is hereby corrected as shown below:

Col. 5, line 59, delete "5-dihydro-4omethyl", insert --5-dihydro-4-methyl--

Col. 6, line 38, delete "fluazifop-Pobutyl", insert --fluazifop-P-butyl--

Signed and Sealed this

Twentieth Day of October, 1998

Attest:

BRUCE LEHMAN

*Attesting Officer*     *Commissioner of Patents and Trademarks*